US012779366B2

(12) United States Patent
Saklar Ayyildiz et al.

(10) Patent No.: US 12,779,366 B2
(45) Date of Patent: Nov. 3, 2026

(54) CARNOSIC ACID, CARNOSOL AND ROSMARINIC ACID ISOLATION METHOD

(71) Applicant: TUBITAK, Ankara (TR)

(72) Inventors: Sena Saklar Ayyildiz, Kocaeli (TR); Ebru Pelvan Pelitli, Kocaeli (TR); Bülent Karadeniz, Kocaeli (TR)

(73) Assignee: TUBITAK, Ankara (TR)

( * ) Notice: Subject to any disclaimer, the term of this patent is extended or adjusted under 35 U.S.C. 154(b) by 951 days.

(21) Appl. No.: 17/638,067

(22) PCT Filed: Jul. 29, 2020

(86) PCT No.: PCT/IB2020/057159

§ 371 (c)(1),
(2) Date: Feb. 24, 2022

(87) PCT Pub. No.: WO2021/038340

PCT Pub. Date: Mar. 4, 2021

(65) Prior Publication Data

US 2022/0313655 A1 Oct. 6, 2022

(30) Foreign Application Priority Data

Aug. 26, 2019 (TR) ................................ 2019/12820

(51) Int. Cl.

| | |
|---|---|
| ***A61K 31/366*** | (2006.01) |
| ***A61K 31/192*** | (2006.01) |
| ***A61K 31/216*** | (2006.01) |
| ***A61K 36/537*** | (2006.01) |

(52) U.S. Cl.

CPC .......... *A61K 31/366* (2013.01); *A61K 31/192* (2013.01); *A61K 31/216* (2013.01); *A61K 36/537* (2013.01)

(58) Field of Classification Search

CPC .. A61K 31/366; A61K 31/192; A61K 31/216; A61K 36/537; A61K 2236/00; A61K 36/53; B01D 11/0265; B01D 11/0288; B01D 15/265; B01D 11/028; C07C 51/47; C07C 62/32; C07C 67/56; C07C 69/732; C07D 493/08

See application file for complete search history.

(56) References Cited

U.S. PATENT DOCUMENTS

| | | | | |
|---|---|---|---|---|
| 3,950,266 | A | 4/1976 | Chang et al. | |
| 5,256,700 | A | 10/1993 | Aeschbach et al. | |
| 5,859,293 | A | 1/1999 | Bailey et al. | |
| 9,376,351 | B2 | 6/2016 | Nahas et al. | |
| 2003/0049332 | A1 | 3/2003 | Greaves et al. | |
| 2022/0313655 | A1* | 10/2022 | Saklar Ayyildiz | A61K 36/53 |
| 2024/0245741 | A1* | 7/2024 | Khadhraoui | B01D 11/0257 |

FOREIGN PATENT DOCUMENTS

| | | |
|---|---|---|
| CN | 102199092 | 9/2011 |
| CN | 102432469 | 5/2012 |
| CN | 102115442 | 10/2013 |
| CN | 103319495 | 3/2016 |
| CN | 108070453 | 5/2018 |
| CN | 108338406 | 7/2018 |
| CN | 108420849 | 8/2018 |
| CN | 104939267 | 7/2019 |
| WO | 2000049115 | 8/2000 |

OTHER PUBLICATIONS

Oliveira, G.A.R., et al., Multiresponse optimization of an extraction procedure of carnosol and rosmarinic and carnosic acids from rosemary, 2016, Food Chem, 211:465-473, 9 pages. <http://dx.doi.org/10.1016/j.foodchem.2016.05.042>. (Year: 2016).*

Handa, S.S., et al., Extraction Technologies for Medicinal and Aromatic Plants, 2008, International Centre for Science and High Technology, 263 pages. (Year: 2008).*

Tang, W., et al., Preparative separation and purification of rosmarinic acid from perilla seed meal via combined column chromatography, 2014, J Chromatog B, 947-948:41-48, 8 pages. <dx.doi.org/10.1016/j.jchromb.2013.12.007>. (Year: 2014).*

Zibetti, A.W., et al., Solvent extraction and purification of rosmarinic acid from supercritical fluid extraction fractionation waste: Economic evaluation and scale-up, 2013, J Supercri Fluids, 83:133-145, 14 pages. <dx.doi.org/10.1016/j.supflu.2013.09.005>. (Year: 2013).*

Montag, How to filter your plant extracts, macerated oil, and tinctures, 2015, Swettis Beauty Blog, 8 pages. <https://skinchakra.eu/blog/archives/355-How-to-filter-your-plant-extracts,-macerated-oils-and-tinctures.html>. (Year: 2015).*

"Obtention and characterization of rosemary and ash tree seed extracts and study of their preventive effects on metabolic disorders" (by Sixto Alvin Ibarra Rober, 2011).

* cited by examiner

*Primary Examiner* — Aaron J Kosar
*Assistant Examiner* — Jennifer Lynn Cain
(74) *Attorney, Agent, or Firm* — Crose Law LLC; Bradley D. Crose

(57) ABSTRACT

The invention relates to a method of separation by fractionalization of the antioxidant active ingredients of Rosemary plant, which are the diterpenes Carnosic acid and Camosol and the phenolic acid Rosmarinic Acid, through column chromatography method. The production process involves the passage of rosemary extract, which is obtained in/with a proper solvent, through a column packed with a suitable packing material, the separation of the part rich in carnosic acid and carnosol, and the obtainment of a deodorized product in powder form after drying. During the process, another extract containing rosmarinic acid with high antioxidant activity is also obtained. The invention thus allows the use of an extract rich in carnosic acid and carnosol and another extract containing rosmarinic acid—which are obtained at once with no need for additional processes like acidification, precipitation, membrane filtration or deodorization—in food, pharmaceutical and cosmetic sector applications.

3 Claims, 1 Drawing Sheet

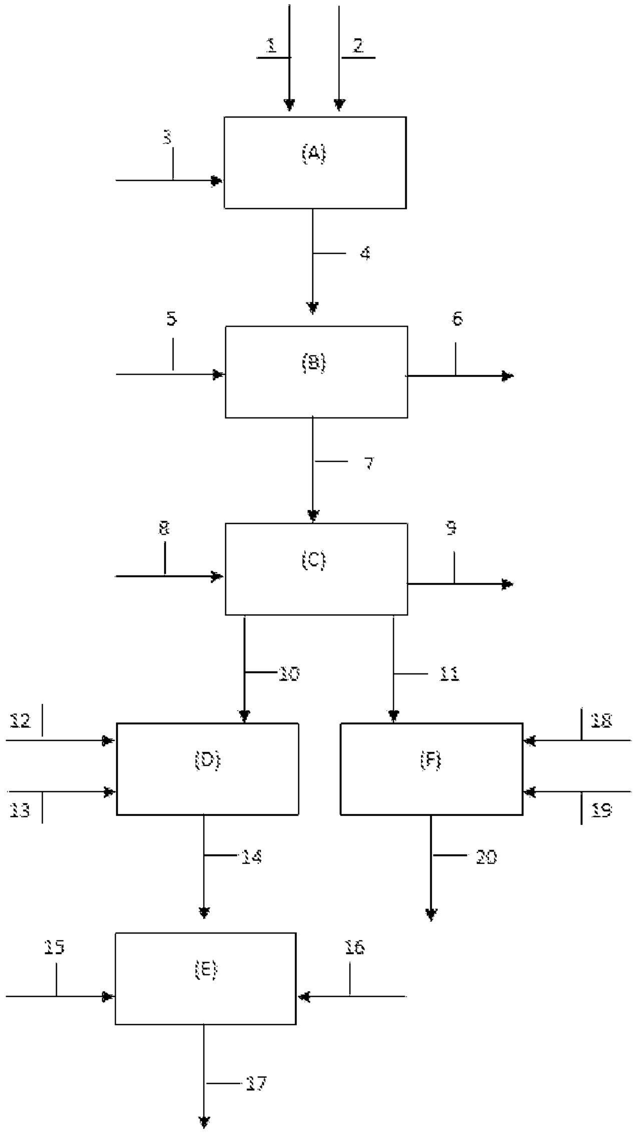
1
2
3
(A)
4
5
(B)
6
7
8
(C)
9
10
11
12
(D)
13
(F)
18
19
14
20
15
(E)
16
17

CARNOSIC ACID, CARNOSOL AND ROSMARINIC ACID ISOLATION METHOD

TECHNICAL FIELD OF THE INVENTION

The invention relates to a method of separation by fractionalization of the antioxidant active ingredients of Rosemary plant (*Rosmarinus officinalis*), which are the diterpenes Carnosic acid and Carnosol and the phenolic Rosmarinic Acid, through column chromatography.

PRIOR ART

There are various methods of extraction and purification in the literature to produce rosemary extract with high content of carnosic acid and carnosol, which are used as natural antioxidants in food and cosmetics industries. These methods allow the production of extracts containing carnosic acid, carnosol and rosmarinic acid in varying amounts and concentrations. These extracts are used in many products owing to their antioxidant properties; however, the amounts of active ingredients decrease proportionally during production processes. Thus, it would be a great advantage to be able to produce extracts in high concentrations with practical methods.

Within the scope of prior art,

The US patent No. U.S. Pat. No. 5,256,700A relates to the extraction of rosemary with an apolar solvent or mixture of solvents and the separation of carnosic acid by passing the extract through a column packed with an only carnosic acid-selective adsorbent together with a polar solvent. In the column, polyamide or polyvinylpyrrolidone is used as adsorbent and only carnosic acid is separated from the extract.

In the US patent No. U.S. Pat. No. 5,859,293A, rosemary is extracted with a water-miscible solvent where the pH of the solution is adjusted to a level between 7 and 10; and the compounds other than carnosic acid are precipitated. The pH of the solution is increased with sodium carbonate, sodium bicarbonate or ammonium hydroxide. By filtration or centrifugation, the carnosic acid is separated from the precipitated compounds. Then, carnosic acid is precipitated by adding sulphuric acid or acetic acid to the solvent containing carnosic acid and only the carnosic acid is separated from the solution either by filtration or centrifugation.

In the US patent No. U.S. Pat. No. 9,376,351B2, rosmarinic acid, carnosic acid and carnosol, which are the water and oil-soluble antioxidant compounds of the rosemary plant, are extracted using a mixture of water and ethyl alcohol. By evaporating the ethyl alcohol, an extract containing 25% carnosic acid and carnosol is obtained, and by removing the water, an extract containing 9% rosmarinic acid is obtained. The extracts are subjected to a deodorization process.

In the US patent No. US20030049332A1, rosemary is extracted by the use of a blend of tetrafluoroethane, acetone and methanol, and the process yields only an oil-soluble antioxidant.

In the US patent No. U.S. Pat. No. 3,950,266A, rosemary is extracted by the use of a solvent with a low boiling point like ethyl ether, and the solvent is evaporated with molecular distillation or vacuum. The extract is dissolved in a solvent with a high boiling point like cottonseed oil. The mixture is subjected to vapour distillation at 90-95° C. to separate compounds giving odour and aroma. The deodorized extract is then cooled down under vacuum at room temperature; and the antioxidant is obtained as dissolved in oil.

In the international patent application No. WO2000049115A2, the plants from Labiatae family are extracted at 0-100° C. with an organic solvent, and then, the solvent is evaporated. The concentrated solution is saturated with inert nitrogen gas at 0.1-0.5 bar in adsorption column and transferred to atmospheric pressure. The concentrated solution is re-extracted with water vapor, and the extract is filtered and separated from ethyl alcohol, water and essential oil. So, compounds (polyphenols) with antioxidant properties are obtained.

In the Chinese patent No.CN108070453A, the deoiled rosemary is extracted with ethanol-water mixture and passed through a ceramic membrane. The aqueous and solid parts are separated by centrifugation, and the solid part is extracted again with ethanol-water mixture. With the evaporation of ethyl alcohol, the carnosic acid in the aqueous part is obtained by drying. The aqueous part separated by centrifugation is dried to obtain rosmarinic acid. Filtration and centrifugation steps are repeated at least for 3 times. As a result, 5.06% rosmarinic acid and 30.26% carnosic acid are obtained.

In the Chinese patent No.CN102432469A, rosemary is extracted with 60% ethanol solution, subjected to filtration and ascorbic acid addition steps and passed through a ceramic membrane. It is passed through LSA-10 column by the use of petroleum ether and ethyl acetate. After the concentration and drying steps, rosmarinic acid and ursolic acid are separated.

In the Chinese patent No.CN102199092A, rosemary is extracted with ethanol in ultrasonic counter-current extractor, filtering the obtained solution, and further treating the liquid filtrate with macroporous adsorption resin, and the solid filter cake by a CO2 supercritical extraction process. After contact with macroporous resin, the latter is eluted with a gradient of ethanol ranging from 40% to 80%; the eluted fractions are then concentrated under reduced pressure after spray drying, and crystallized.

In the Chinese patent No. 103319495B, a method for preparing carnosol is described, the method comprising an extraction of rosemary leaves with a lipophilic organic solvent, typically ethanol, and filtering the obtained extract, treating with a macroporous resin and eluting with 90% ethanol solution, evaporating to concentrate, filtering and crystallizing.

In the Chinese patent No. 108420849A, a method of preparation of a rosemary extract which comprises cleaning and drying rosemary, oven-drying at 40-50° C., high-speed crushing, and sieving with a 40-mesh sieve; extracting with 85-95% ethanol, and concentrating to obtain an alcohol-free taste ethanol extract concentrated solution; diluting the ethanol extract concentrated solution with water, petroleum ether, ethyl acetate, and water-saturated n-butanol, extracting, and concentrating to obtain petroleum ether extract, ethyl acetate extract, and n-butanol extract; then dissolving the ethyl acetate extract in water, and filtering. The obtained product is passed onto a macroporous resin which is eluted stepwise with a 10% ethanol solution and then with a 90% ethanol solution.

In the doctoral dissertation on "Obtention and characterization of rosemary and ash tree seed extracts and study of their preventive effects on metabolic disorders" (by Sixto Alvin IBARRA ROBER, 2011), rosemary is extracted with acetone, and the solid and liquid phases are separated by centrifugation. According to the method specified in the US patent No.U.S. Pat. No. 5,859,293, base and then acid are added to the liquid phase; and carnosic acid is precipitated and separated by drying process. An extract containing 20% carnosic acid is obtained. Rosemary is extracted with water and acid is added to the extract. Rosmarinic acid is separated by fractionating in a column containing Styrene-diviniyl-benzene XAD-16 and an extract with 20% rosmarinic acid is obtained.

Technical Problem to Be Solved By the Invention

When it is desired to reach the values of carnosic acid and carnosol recommended by EFSA for rosemary extract to have antioxidant properties, problems are encountered in the product to which the extract is added, like turbidity and rosemary aroma dominance. In order to solve such problems, the carnosic acid and carnosol concentrations obtained from rosemary need to be increased. In this way, the amount of rosemary extract to be added to a product will be reduced, on the other hand, the amounts of carnosic acid and carnosol will reach the values recommended by EFSA. Owing to this invention, the amounts of EFSA-recommended carnosic acid and carnosol—which were in a range between 3 and 26% (30 mg/g-260 mg/g) in previously used extraction methods—are increased up to 42 to 48%. The final product does not have a dominant rosemary odour. Therefore, it falls into deodorized product group. The efficiency is increased owing to the process conditions in the column chromatography method used in the invention (packing material, mobile phase flow program) and the conditions of sample preparation before feeding into the column. In addition, unlike other methods in the literature, surprisingly, carnosic acid, carnosol and rosmarinic acid are produced at once using the same column and the same mobile phase at a higher purity.

Also, ethanol, which is used as a solvent in the extraction of carnosic acid and carnosol from rosemary and in their fractionated separation by column chromatography, is a harmless solvent and environmentally friendly chemical used in foods.

Thanks to the invention, in the fractionating process of carnosic acid and carnosol in column chromatography system, an extract containing rosmarinic acid is obtained as a by-product with pretty high antioxidant properties. The products obtained are of deodorized nature. Rosmarinic acid is an antioxidant that dissolves in water phase and is used in water-based products, while carnosic acid and carnosol are antioxidants that dissolve in oil phase and are generally used in oil-based products.

DESCRIPTIONS OF THE FIGURES

The flow diagram of the purification process designed in line with the purpose of this invention is shown in the attached FIG. 1.

FIG. 1. Carnosic acid, carnosol and rosmarinic acid isolation process

DESCRIPTIONS OF THE REFERENCES IN THE FIGURES (A) De-oiled rosemary extraction step
1. De-oiled rosemary
2. 50% ethanol:water solution
3. Heating
4. Solid-liquid extract (B) Filtration step
5. Vacuum
6. Insoluble solid matter
7. Liquid extract (C) Step of passing through a macro-porous adsorbent-containing column
8. Gradient mobile phase consisting of water and/or ethanol
9. Waste
10. Eluent containing rosmarinic acid (Liquid extract containing rosmarinic acid)
11. Eluent containing carnosic acid and carnosol (Liquid extract containing carnosic acid and carnosol)

(D) First evaporation step
12. Temperature
13. Vacuum
14. Liquid extract rich in rosmarinic acid (E) Freeze drying step
15. Vacuum
16. Cooling
17. Rosmarinic acid extract (F) Second evaporation step
18. Temperature
19. Vacuum
20. Carnosic acid+carnosol extract Explanation of the Invention The invention aims to produce rosemary extract rich in carnosic acid and carnosol which are used as natural antioxidants in food and cosmetic sectors. To this end, the liquid extract obtained from rosemary plant with ethanol-water mixture is fractionated by column chromatography method using a suitable packing material and mobile phase flow program; and a deodorized extract is obtained containing 42-48% carnosic acid and carnosol. In addition to the carnosic acid and carnosol extract, an extract containing rosmarinic acid is also obtained in the column chromatography system. In this method, by making use of the suitable solution (ethanol-water) and solvent ratio (50%) for the most efficient extraction of the active ingredients from rosemary and taking advantage of the active ingredients' differences of solubility in water and ethanol and their adsorption affinities against the packing material, it is made possible to produce an extract containing 42-48% carnosic acid and carnosol and another product containing 7-8% rosmarinic acid with high antioxidant activity, at once with a more practical method compared to other methods. The liquid extracts obtained from column chromatography are dried and powdered, in rotary evaporator or lyophilizer, depending on their ethanol and water content.

Process flow diagram of the developed method is shown in FIG. 1.

1—De-oiled rosemary (1) is extracted with 50% ethanol: water (v:v) solution (2). Extraction method is ultrasonic water bath at 60° C. for 20 min (3).

2—The extract (4) is separated from solid matter (6) by vacuum filtration (5). The filtered liquid extract is filtered for a second time using a fine filter with 1—5 micrometer pore diameter (B).

3—The liquid extract obtained (7) is now ready for feeding into the column (C) containing a macro-porous adsorbent. Before feeding the liquid extract (7) into the column packed with styrene divinylbenzene adsorbent and water, deionized water (8) as mobile phase is passed through the column and the eluent from the column goes to waste (9).

4—The liquid extract (7) is fed into the conditioned column. Within this time period, the eluent observed at 284 nm wavelength corresponding to peak-1 zone in chromatogram goes to waste (9).

5—When the feeding of the liquid extract (7) is completed, deionized water (8) as mobile phase is passed through the column and this part goes to waste (9).

6—Then, 50% ethanol-water solution (8) is passed through the column as mobile phase; meanwhile the eluent corresponding to the peak-2 zone (liquid extract containing rosmarinic acid) (10) is collected for evaporation.

7—In the next step, 99% ethanol (8) is passed through the column as mobile phase, and in the meantime, the eluent corresponding to the peak-3 zone (liquid extract containing carnosic acid and carnosol) (11) is collected for evaporation.

8—The column is washed away and cleaned by passing ethanol (8) as mobile phase so that it becomes ready for the next run. Then, deionized water (8) is passed as mobile phase and the column becomes ready for the next run (C).

9—The eluent (10) corresponding to the peak-2 zone in the column chromatography contains 50% ethanol-water, while the eluent (11) corresponding to the peak-3 zone contains only ethanol. The eluent corresponding to the peak-2 zone is subjected to vacuum (13) in rotary evaporator at 40° C. (12) until the ethanol evaporates completely. The remaining aqueous part (14) is freeze dried at lyophilizer (15), dried (E) under vacuum (16), and rosmarinic acid extract (17) is obtained. Since the eluent (11) corresponding to the peak-3 zone is composed of ethanol only, it is subjected to vacuum (19) in rotary evaporator at 40° C. (18) until it dries completely. As a result of second evaporation step (F), an extract of carnosic acid and carnosol (20) is obtained in powder form.

EXAMPLE 200 grams of deoiled rosemary is extracted with 2 liters of (50% ethanol:water, v:v) solution. Extraction method is ultrasonic water bath at 60° C. for 20 min. The extract is separated from solid matter by vacuum filtration. The filtered liquid extract is filtered for a second time using a fine filter with 1-5 micrometer pore diameter.

The liquid extract obtained is now ready for feeding into the column containing a macro-porous adsorbent. Before feeding the liquid extract into the column packed with styrene divinylbenzene Diaion HP20 adsorbent and water; deionized water as mobile phase in the amount of 0.2 times of the column volume is passed through the column and the eluent from the column goes to waste. The conditioned column is fed with liquid extract in the amount of 1.5 times of the column volume. Within this time period, the eluent observed at 284 nm wavelength corresponding to peak-1 zone in chromatogram goes to waste. When the feeding of the liquid extract is completed, deionized water as mobile phase in the amount of the column volume is passed through the column and this part goes to waste. Then, 50% ethanol-water solution as mobile phase in the amount of 2 times of the column volume is passed through the column; and the eluent corresponding to the peak-2 zone (liquid extract containing rosmarinic acid) is collected for evaporation. In the next step, 99% ethanol as mobile phase in the amount of 2 times of the column volume is passed through the column, meanwhile, the eluent corresponding to the peak-3 zone (liquid extract containing carnosic acid and carnosol) is separately collected for evaporation. The column is washed away and cleaned by passing ethanol as mobile phase in the amount of the column volume, so that it becomes ready for the next run. Then, deionized water is passed as mobile phase in the amount of the column volume and the column becomes ready for the next run.

The eluent corresponding to the peak-2 zone in the column chromatography contains 50% ethanol-water, while the eluent corresponding to the peak-3 zone contains only ethanol. The eluent corresponding to the peak-2 zone is subjected to vacuum in rotary evaporator at 40° C. until the ethanol in it evaporates completely. The remaining aqueous part is freeze dried at lyophilizer, dried under vacuum, and rosmarinic acid extract is obtained. Since the eluent corresponding to the peak-3 zone is composed of ethanol only, it is subjected to vacuum in rotary evaporator at 40° C. until it dries completely. As a result of this process, an extract of carnosic acid and carnosol is obtained in powder form.

Analysis results on total phenolic compounds and antioxidant activity of carnosic acid, carnosol and rosmarinic acid extracts in dried powder form are given in Table 1 below.

TABLE 1

Active ingredients and antioxidant activities of extracts

| | Amount of active ingredient, mg/100 mg | Total phenolic compounds, mg GAE/100 mg | DPPH, $IC_{50}$ value, mg extract/ml | ABTS, mg TE/100 mg |
|---|---|---|---|---|
| Extract containing carnosic acid and carnosol | 44.09 | 22.38 | 0.19 | 53.23 |
| Extract containing rosmarinic acid | 7.42 | 29.00 | 0.21 | 50.65 |

Active ingredient amounts: For the extract containing carnosic acid and carnosol, the amount is determined with the sum of carnosic acid and carnosol content, whereas, for the extract containing rosmarinic acid, the amount is determined with the rosmarinic acid content per 100 mg extract.
Total phenolic compounds: Results are given in mg gallic acid equivalent/100 mg extract.
DPPH: (2,2-diphenyl-1-picrylhydrazyl) radical scavenging capacity
Results are given in $IC_{50}$ (sample amount required to halve initial DPPH concentration in mg extract/ml solution).
ABTS: Trolox-equivalent (6-Hydroxy-2,5,7,8-tetramethylchromane-2-carboxylic acid) antioxidant capacity (TEAC—ABTS)
Results are given in mg Trolox-equivalent/100 mg extract.

This method makes it possible to produce deodorized extracts rich in carnosic acid and carnosol, by using plant species such as rosemary (*Rosmarinus officinalis*) and sage (*Salvia fruticosa*) from the Labiatae (Lamiaceae) family.

It is possible to use both deoiled rosemary and oil-containing rosemary, however, in case of oil-containing rosemary use, efficiency may decrease.

For the extraction of active ingredients, the rosemary: solvent (solid:liquid) ratio can be in the range from 1:1 to 1:200.

The solvent to be used for the extraction of active ingredients can be ethanol as well as other polar and apolar solvents like methanol, acetone and hexane. The ratio of the solvent used for the extraction of active ingredients can range from 5% to 100%.

During the feeding of the extract into the column, the ratio of extract:column volume can range from 0.01 to 5.

During fractionating by column chromatography method, it is possible to use a column chromatography system or apparatus.

As the column packing material, it is possible to use styrene divinylbenzene Diaion HP20, as well as macroporous polyamide, polyacrylate, polymethacrylate and polyvinylpyrrolidone adsorbents.

During fractionating by column chromatography, as mobile phase, it is possible to use ethanol:water, as well as polar and apolar solvents like methanol, acetone and hexane.

In the mobile phase flow program, it is possible to start with 100% water and switch to 50% ethanol:water flow and finally to 100% ethanol flow; or instead of a stepwise transition, it is possible to switch directly from 100% water to 100% ethanol.

The obtained liquid extracts could be dried in rotary evaporator or lyophilizer, as well as in a vacuum dryer, vacuum oven or spray dryer.

If desired, the active ingredient amounts of the extracts can be increased by using a second column.

Industrial Application of the Invention

The extracts containing carnosic acid, carnosol and rosmarinic acid can be used in food, pharmaceutical and cosmetic products both directly and by encapsulation.

The invention claimed is:

1. A method for isolation of carnosic acid, carnosol, and rosmarinic acid, comprising the sequential steps of:

i. extracting de-oiled rosemary in an ultrasonic water bath at 60° C. for 20 min with a 50% v/v aqueous ethanolic solution to obtain a de-oiled rosemary extract;

ii. filtering the de-oiled rosemary extract through coarse filter paper by vacuum to remove insoluble material and then through a filter with a 1-5 μm pore diameter to obtain a filtered liquid extract;

iii. passing deionized water through a macro-porous adsorbent-containing column as a mobile phase to obtain a prepared column;

iv. feeding the filtered extract into the prepared column in an amount of 0.01 to 5 times of the column volume, wherein an eluent with a wavelength of 284 nm corresponds to waste;

v. passing a 50% aqueous ethanolic solution through the column as a mobile phase and collecting an eluent comprising rosmarinic acid, wherein the ethanol is evaporated from the eluent comprising rosmarinic acid under vacuum in a rotary evaporator, vacuum dryer, or vacuum oven to obtain an aqueous rosmarinic acid extract;

vi. freeze drying the aqueous rosmarinic acid extract to obtain a deodorized powdered rosmarinic acid extract; and vii. passing a 99% ethanol solution through the column as a mobile phase and collecting an eluent comprising carnosic acid and carnosol, wherein all of the ethanol is evaporated from the eluent in a rotary evaporator at 40° C. to obtain a powdered extract comprising carnosic acid and carnosol.

2. The isolation method according to claim 1, wherein at step iv the filtered extract is 1.5 times the column volume.

3. The isolation method according to claim 1, wherein the macro-porous adsorbent-containing column at step iii is selected from the group consisting of styrene divinylbenzene, macro-porous polyamide, polyacrylate, polymethacrylate, and polyvinylpyrolidone adsorbents.

* * * * *